US012806329B2

(12) United States Patent
Serafini et al.

(10) Patent No.: US 12,806,329 B2
(45) Date of Patent: Nov. 24, 2026

(54) EAR CLEANING DEVICE

(71) Applicant: Miocolibri SRLS, Venice (IT)

(72) Inventors: Massimo Alessio Serafini, Rome (IT); Alessandro Paulis, Milan (IT)

(73) Assignee: Miocolibri SRLS, Milan (IT)

( * ) Notice: Subject to any disclaimer, the term of this patent is extended or adjusted under 35 U.S.C. 154(b) by 668 days.

(21) Appl. No.: 18/246,980

(22) PCT Filed: Sep. 28, 2021

(86) PCT No.: PCT/IB2021/058830
§ 371 (c)(1),
(2) Date: Mar. 28, 2023

(87) PCT Pub. No.: WO2022/070026
PCT Pub. Date: Apr. 7, 2022

(65) Prior Publication Data

US 2023/0405214 A1 Dec. 21, 2023

(30) Foreign Application Priority Data

Oct. 2, 2020 (IT) ........................ 102020000023245

(51) Int. Cl.
*A61M 3/02* (2006.01)
*A61M 25/10* (2013.01)

(52) U.S. Cl.
CPC ....... *A61M 3/0295* (2013.01); *A61M 25/1002* (2013.01); *A61M 2205/0216* (2013.01); *A61M 2210/0662* (2013.01)

(58) Field of Classification Search
CPC .............. A61F 13/2022; A61F 13/2028; A61F 13/2031; A61F 13/2034; A61F 13/2048;
(Continued)

(56) References Cited

U.S. PATENT DOCUMENTS

2010/0312198 A1* 12/2010 Guidi .................... A61F 11/006 606/162

FOREIGN PATENT DOCUMENTS

CN 201205321 Y * 3/2009 ............ A61F 11/006
CN 108125744 A * 6/2018 ............ A61F 11/006
(Continued)

OTHER PUBLICATIONS

Patent Cooperation Treaty International Search Report for International Application No. PCT/IB2021/058830.
(Continued)

*Primary Examiner* — Katherine M Shi
(74) *Attorney, Agent, or Firm* — Mark Malek; Widerman Malek, PL

(57) ABSTRACT

An ear cleaning device comprising a fluid dispenser in communication with a hollow cleaning body. The hollow cleaning body is elongated according to a relative longitudinal axis. The cleaning body includes an insertion portion configured to assume a resting configuration in which it is at least partially insertable into the ear canal of an ear, and an expanded configuration in which it has an increased volume due to expansion by fluid provided by the fluid dispenser. The insertion portion includes a plurality of lobes which are elongated according to the longitudinal axis and form convex portions towards the outside of the insertion portion. The insertion portion also includes connecting walls between the lobes which are developed according to the longitudinal axis forming grooves between the lobes.

11 Claims, 5 Drawing Sheets

(58) Field of Classification Search
CPC ........ A61F 11/006; A61F 13/38; A61B 17/24; A61B 2017/246; A61M 2210/0618; A61M 2210/0662; A61M 3/0262; A61M 3/0295; A61M 25/1002; A61M 2025/1004; A61M 2205/0216
See application file for complete search history.

(56) References Cited

FOREIGN PATENT DOCUMENTS

| | | | | | |
|---|---|---|---|---|---|
| DE | 2048798 | A1 | | 4/1972 | |
| DE | 9409240 | U1 | | 11/1994 | |
| DE | 19529117 | A1 | * | 2/1997 | ............ A61F 11/006 |
| EP | 0234061 | A1 | | 9/1987 | |
| EP | 1407735 | A1 | | 4/2004 | |
| KR | 200379270 | Y1 | * | 3/2005 | ............... A47K 7/00 |
| KR | 20080008757 | A | * | 1/2008 | ............ A61F 11/006 |

OTHER PUBLICATIONS

Patent Cooperation Treaty Written Opinion by International Search Authority for International Application No. PCT/IB2021/058830.

* cited by examiner

EAR CLEANING DEVICE

RELATED APPLICATIONS

This application is a national phase application of and claims priority under 35 U.S.C. § 371 of PCT Application Serial No. PCT/IB2021/058830 filed on Sep. 28, 2021 and titled EAR CLEANING DEVICE which in turn is a PCT International Application of and claims priority under PCT Article 8 of Italian Patent Application Serial No. 102020000023245 filed on Oct. 2, 2020 and titled Dispositivo per la pulizia delle orecchie (English translated title: EAR CLEANING DEVICE). The content of these applications is incorporated herein by reference, except for where the content therein conflicts with the content herein.

TECHNICAL FIELD

The present invention relates to ear cleaning devices.

STATE OF THE ART

As is known, the cleaning of the ears is essential to prevent infections and the formation of earwax plugs, and requires particular attention in the execution because it is not without risk to the parts of the ear, such as the eardrum, more internal than the auricle.

This cleaning is often carried out using a cotton swab (or Q-tip) which, however, has well-known contraindications, because it exposes the earwax to the risk of being pushed inside the ear canal and to the possibility of damaging the eardrum. Moreover, due to an incorrect disposal by the user, cotton buds accumulate in sewage treatment plants and water courses.

Several types of ear cleaning devices have been proposed to replace Q-tips.

One type of device involves the use of a soft, helical-shaped tip that is inserted into the ear and rotated (manually or electrically) to remove earwax.

Other types of devices, such as the so-called auricular syringe, require the introduction of water or emollient liquids into the ear canal.

A device has also been proposed that relies on the vibration (caused by an electric motor) of a tip introduced into the ear canal, which would cause fragmentation of the earwax, and subsequent aspiration of the same.

According to another typology, the device consists of a rod made of biocompatible plastic having at both ends a silicone head equipped with protuberances intended to facilitate the removal of earwax; this device is used in a manner similar to how the cotton bud is used.

Document CN105982788 describes a cleaning device comprising a pressure air pump connected to an internally hollow terminal body having soft hairs on its surface. In use, the terminal body is inserted into the ear canal and then pressure is applied to the pump causing said body to expand so that the soft hairs contact the walls of the ear canal removing ear wax. According to that document, after the terminal body is deflated, it is pulled out of the ear removing the earwax that remains trapped between the soft hairs.

Document DE2048798 describes an ear cleaning device comprising a rubber ball connected via a channel to a free end intended to expand when air is pushed from the rubber ball. Solid “warts” (indicated by 6 in document DE2048798) are disposed on the free end to capture earwax.

Document EP0234061 describes an instrument for cleaning the external ear canal consisting of a stem and a pear-shaped head. There is a set of protruding ribs on the head for removing earwax.

SUMMARY OF THE INVENTION

The purpose of the present invention is to propose an ear cleaning device, based on the use of an air-expandable cleaning body, which is an alternative to the one known and mentioned above and which, in particular, is efficient in the cleaning action while also offering full safety for the user in its use.

It is an object of the present invention an ear cleaning device as defined by claim 1 and particular embodiments thereof described by dependent claims 2-10.

BRIEF DESCRIPTION OF THE DRAWINGS

The constructional and functional features of the invention may be better understood from the following detailed description, in which reference is made to the accompanying drawing plates representing some preferred and non-limiting forms of implementation, wherein.

DETAILED DESCRIPTION

FIGS. 1-9 show an example of an ear cleaning device 1 comprising an air nozzle 2 and a cleaning body 3 connected to the air nozzle 2. According to the described example, the cleaning device 1 may further comprise a junction member 4 of the nozzle 2 to the cleaning body 3.

Figure 2:
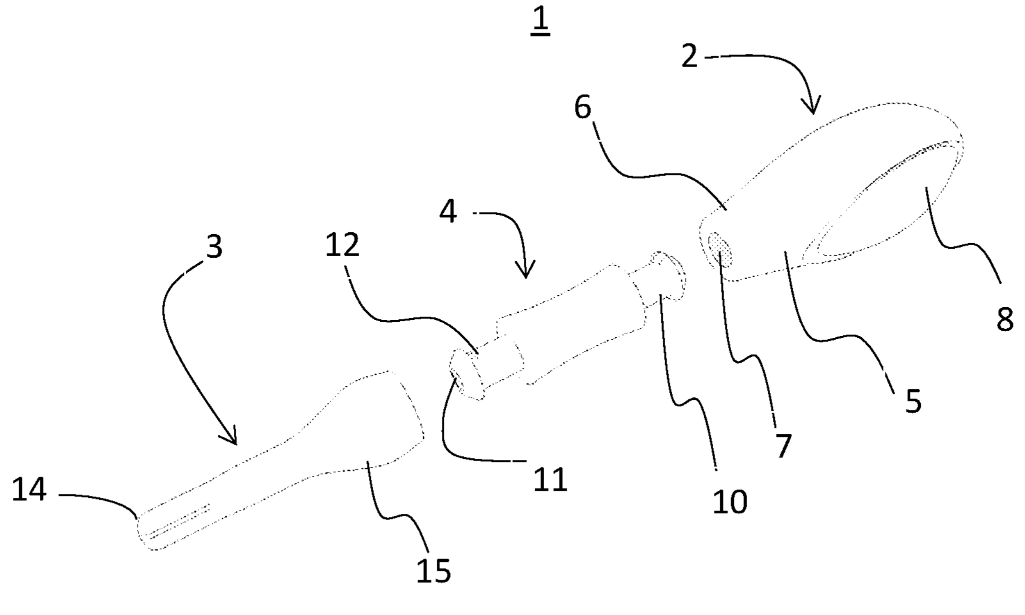
FIG. 2 shows a front perspective view of said device, in the de-assembled configuration.
Figure 3:
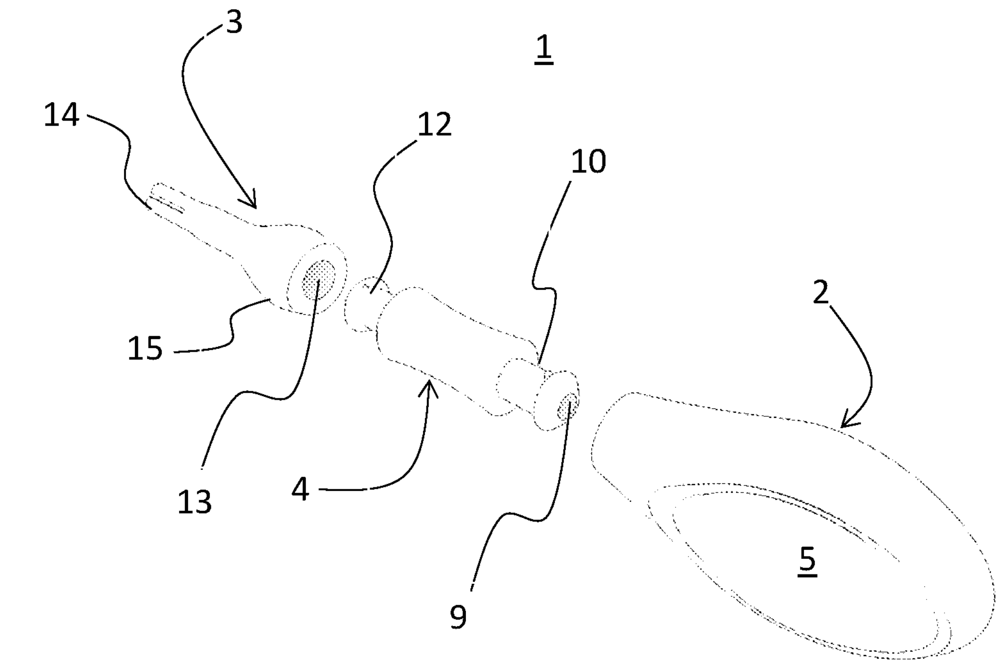
FIG. 3 shows a rear perspective view of said device, in the de-assembled configuration.

The dispenser 2 is configured to transfer pressurized air to the cleaning body 3. In accordance with a preferred embodiment, the air dispenser 2 is a manual pressure pump 2 comprising a small elastic bag (or ampoule) 5 having an end 6 provided with an air inlet/outlet hole 7 (FIG. 2).

The manual pressure pump 2 is, for example, made of an elastomeric material (such as, for example, latex or rubber) or biocompatible silicone. Advantageously, the outer wall of the elastic bag 5 is shaped to define pressure areas 8 intended to be squeezed between the user's fingers. The manual pressure pump 2 when squeezed delivers air through the hole 7 and, when the manual pressure has ceased, is refilled with air by an elastic expansion of the elastic bag 5.

Note that an air dispenser other than the described manual pressure pump may be provided. For example, a dispenser of the piston type, i.e., a syringe type, may be employed.

The junction element 4, if provided, internally defines an air connection duct open on a first hole 9 (FIG. 3), at a first end 10, and a second hole 11 (FIG. 2), at a second end 12. For example, the first end 10 is configured to be inserted into the hole 7 of the manual pressure pump 2 and the second end 12 is configured to be inserted into a further hole 13 provided by the cleaning body 3. According to a particular embodiment, the first and second ends 10 and 12 have a relative mushroom-shaped head so as to avoid an undesirable separation from the manual pressure pump 2 and the cleaning body 3.

It should be noted that the junction element 4 may be removably attached to the cleaning body 3 and the dispenser 2 in other ways than those described, and for example, such as providing for the use of ferrules, sealing bands or by screwing. Furthermore, it is also possible that the cleaning body 3 and the dispenser 2 may be directly coupled without the use of any joining element.

In particular, the junction element 4 is made of a rigid (preferably, hypoallergenic) plastic material such as, for example, polypropylene. Alternatively, so-called biodegradable plastics may be used.

The cleaning body 3 is internally hollow and is configured to be placed in communication with the air dispenser 2 so as to be able to receive inside itself the air supplied by the latter. This cleaning body develops in length according to a relative longitudinal axis L (FIG. 1).

The cleaning body 3 is such that it assumes a resting configuration in which it is at least partially insertable into the ear canal of one ear and an expanded configuration in which it presents an increased volume due to the air supplied by the nozzle 2. As will also be described later, it is in the expanded configuration that the cleaning body 3 will be able to exert its cleaning function of the ear canal.

Figure 1:
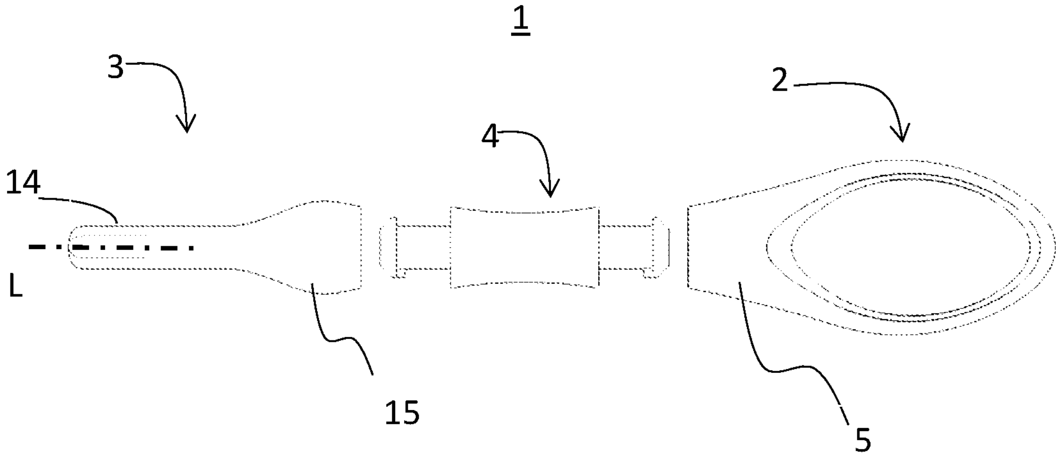
FIG. 1 shows, by a side view and a de-assembled configuration, an ear cleaning device made according to a particular embodiment of the present invention.

In greater detail, the cleaning body 3 comprises an insertion portion 14 having an elongated shape, i.e., developing more along the longitudinal axis L (FIG. 1 and FIG. 2). In addition, the cleaning body 3 includes a fitting portion 15 (in one piece with the insertion portion 14) provided with the aforementioned further hole 13 for inserting the second end 12 of the junction element 4.

Note that the insertion portion 14 includes a plurality of lobes (or bulges) 16 that extend in the direction of the longitudinal axis L; that is, such lobes 16 extend lengthwise in the direction of the longitudinal axis L. Each lobe 16 defines a respective convex wall 17 (i.e., a bulge) that connects to intermediate walls 18 that extend in the direction of the longitudinal axis L and form corresponding grooves between the lobes 16 themselves. The grooves 18 extend in the direction of the longitudinal axis L but are not necessarily parallel to the axis L.

With respect to the number of lobes 16, the example in the figures shows the presence of four lobes 16, but cleaning portions 14 having two lobes, three lobes or a number of lobes greater than four, for example, six, seven or eight lobes, may also be employed.

The cleaning body 3 is soft in that it should be able to swell, adapt to the shape of the ear canal as much as possible, and should not cause damage to the eardrum. In particular, the cleaning body 3 is made of an elastic material such as, for example, biocompatible silicone, or an elastomeric material such as, for example, latex or rubber. The cleaning body 3, or at least the insertion portion 14, may have a smooth outer wall or advantageously be provided with a suitable graininess or embossing that increases its abrasive power.

Figure 7:
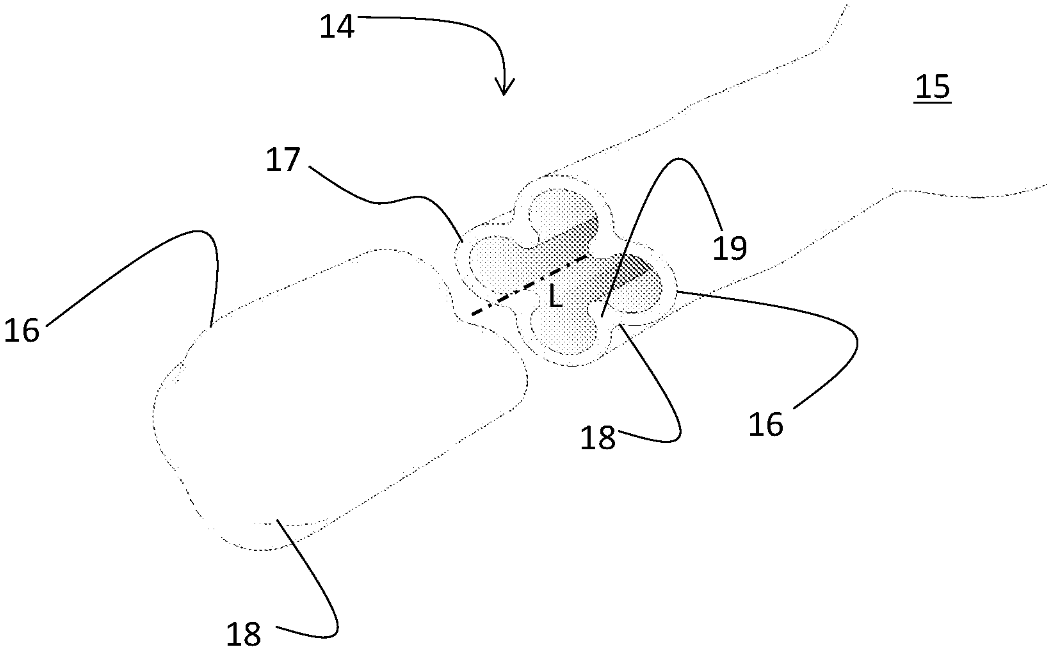
FIG. 7 shows, in a perspective view, a cleaning body of said device having a sectioned insertion portion.

As shown, illustratively, in the sectioned embodiment of FIG. 7, the insertion portion 14 is provided with internal ribs 19 running parallel to each intermediate wall 18 separating the lobes 16.

The above-described shape of the cleaning body 3 allows the lobes 16 to inflate, while the ribs 19 associated with the intermediate walls 18 resist the traction and torsion to which the device 1 is subjected in the expansion and cleaning action. The fitting portion 15 provides a seal with the fitting member 4 (if provided) or directly with the air nozzle 2, to prevent leakage of air from the interior of the cleaning device 1 to the exterior, with drops in internal pressure when inflated.

In addition, the lobe structure has been shown to allow an advantageous increase in the external expandable surface of the cleaning body 3 and also an increase in its abrasive function, compared to what can be obtained with a uniform, non-lobed structure.

In particular, the lobes 16, in extending towards the fitting portion 15 of the cleaning body 3, tend to merge with each other until they form a uniform overall shape, i.e. free of lobes and grooves. In the example considered, the fitting portion 15 of the cleaning body 3 has a spherical or cylindrical type outline (free of grooves and lobes), which is well suited to the function of connecting with the junction element 4.

Furthermore, the fitting portion 15 advantageously has a maximum diameter (distance from the longitudinal axis L) chosen so as to avoid a dangerous, excessive introduction of the cleaning body 3 into the ear canal. For example, the fitting portion 15 has a maximum diameter of about 10.0 mm (dimensions may vary depending on feasibility and the type of user: child, adult and small, medium or large animals).

With respect to possible size values, the insertion portion 14, in a resting configuration, may have, for example, a maximum diameter of between 4.5 mm and 5.00 mm, in particular, between 4.5 mm and 4.8 mm. Note that the values for the diameter of the resting portion of insertion 14 shown above are illustrative only and refer to use for the human ear. Keep in mind that the auditory cord has a fairly variable diameter of up to about 8-9 mm in the adult. Therefore, it is possible to envision different models of the cleaning device 1 having different dimensions.

For example, the thickness of the convex walls 17 (FIG. 7) may be about 0.30 mm, while the overall thickness of the intermediate wall 18 with its associated rib 19 may be about 0.80 mm. In addition, the intermediate walls 18 may have a width of about 0.60 mm. Such values of the thicknesses are only illustrative as other values may be adopted also, but not only, depending on the number of lobes 16.

Figure 4:
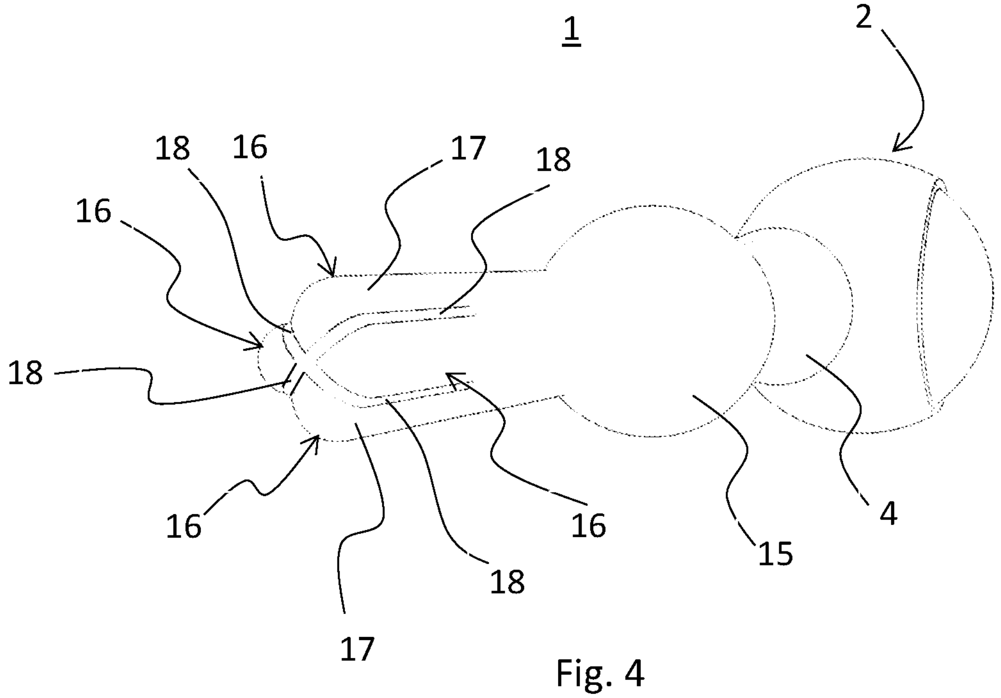
FIG. 4 shows a front perspective view of said device, in an assembled configuration and in rest conditions.
Figure 5:
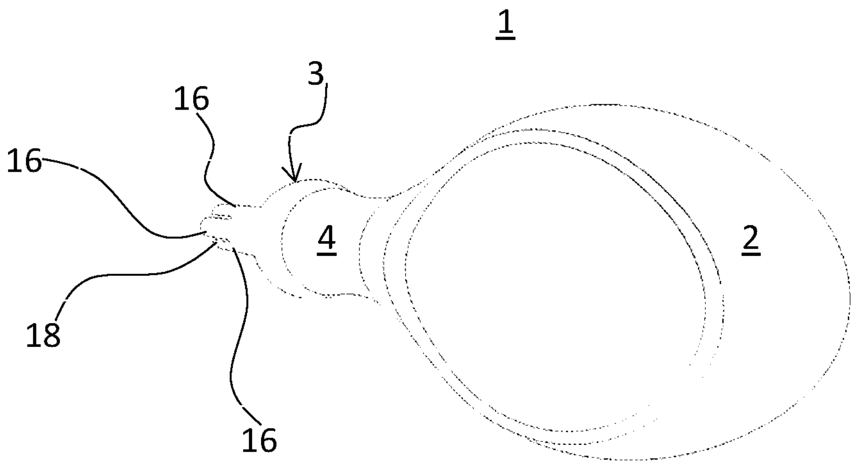
FIG. 5 shows a rear perspective view of said device, in the assembled configuration and in rest conditions.
Figure 6:
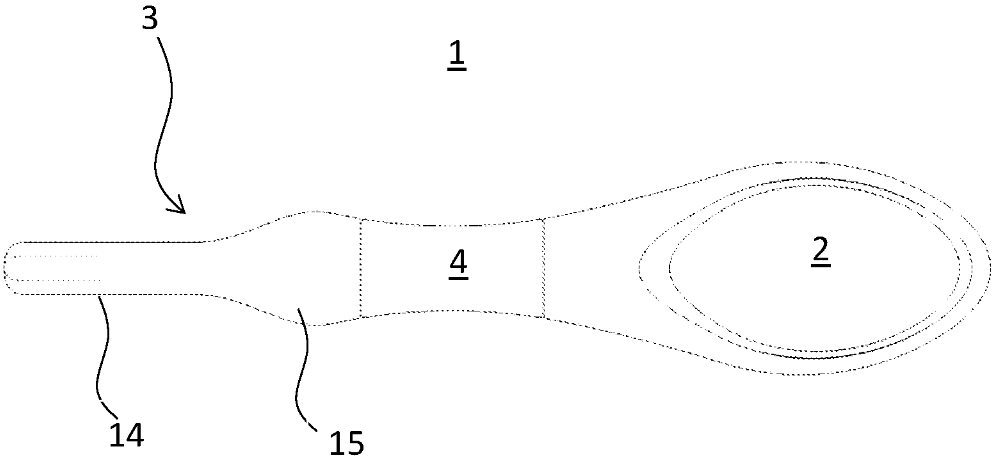
FIG. 6 shows a side view of said device, in assembled configuration and in rest conditions.

The ear cleaning device 1 can be easily assembled by the user by joining the air nozzle 2, the junction member 4, and the cleaning body so that it assumes the configuration shown in FIGS. 4-6. Advantageously, it is also possible to disassemble the ear cleaning device 1 by separating its components, for example, to store it, to wash it, or to replace one of the components.

The ear cleaning device 1, assembled and in the resting configuration (i.e., with the cleaning body 3 un-expanded) is operated by the user grasping it by the manual pressure pump 2 and introducing the insertion portion 14 into the ear canal of one ear.

Next, the user presses his or her fingers on the hand pump 2 and pressurized air escapes from the hole 7 and passes through the inner conduit of the junction element 4 and enters the cleaning body 3.

Figure 8:
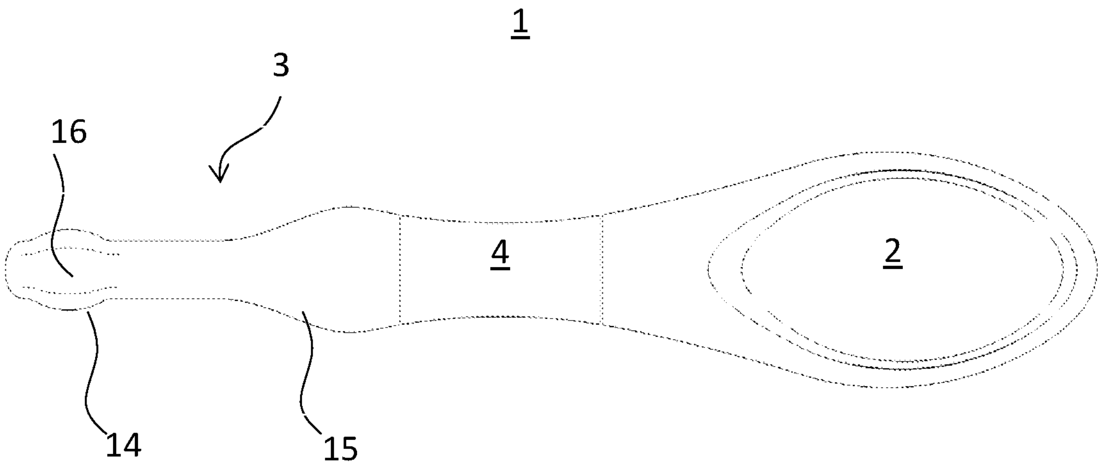
FIG. 8 shows a side view of said device, in the assembled configuration and in a condition of expansion of said cleaning body.
Figure 9:
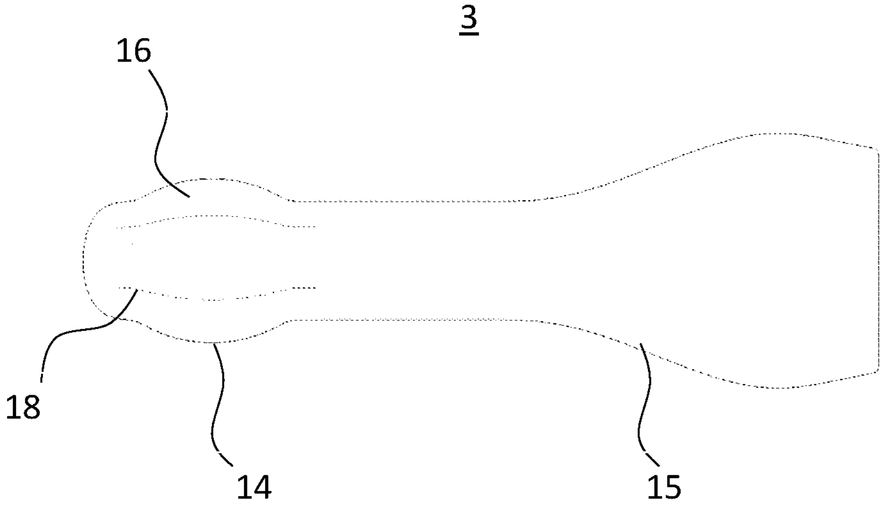
FIG. 9 shows, in a side view, said cleaning body in an expanded condition.

The air entering the cleaning body 3 causes an expansion (i.e., a bulge) of the insertion portion 14, which assumes the configuration shown, illustratively, in FIGS. 8 and 9. The insertion portion 14 when swollen adheres well to the ear canal of the ear. Fitting portion 15 does not expand significantly.

At this point, the user may perform rotations (e.g., in an alternative direction) or small translations of the cleaning device 1 so that the convex surfaces 17 of the swollen lobes 16 can effectively act by rubbing on the ear canal and remove the earwax.

The insertion portion 14, still in the expanded configuration, is extracted from the ear canal so that it removes the abrasion cerumen that has become fixed on its walls as a result of expansion and handling. The cleaning operation may be repeated several times.

Note that the cleaning operation described above may be preceded by the use of an ear canal cleanser.

Note that the lobes 16, together with the grooves 18, allow air to pass outwardly while avoiding both compressing air within the ear during introduction of the insertion portion 14 into the ear canal and creating decompression following removal of the insertion portion 14. This is important for protection of the eardrum.

The cleaning device 1 described is designed specifically for human ear cleaning, but the teachings provided can also be used to make an animal (e.g., dog or cat) ear cleaning device by tailoring the overall geometry of the device to the ear canal of the animal of interest.

It should be noted that although the above description refers to an air dispenser 2, it is also possible to alternatively employ a dispenser of a fluid other than air, such as may be water, but still such that the desired expansion of the insertion portion 14 can be achieved. For example, the aforementioned manual pressure pump or piston dispenser may also be used, with appropriate adaptations, to dispense water in a manner similar to that described for air.

The cleaning device 1 described above is very advantageous.

An advantage is attributable to the fact that the lobes 16 and the grooves 18 allow for adequate structural and sealing resistance during the air compression, device rotation and extraction phases. In addition, the presence of the inflated lobes, which constitute discontinuities, contributes favorably to the cleaning effect of the ear canal.

Another advantage concerns the safety for the user due to the aforementioned ability to avoid compressions or decompressions of air inside the ear canal that could, otherwise, be harmful.

The possibility of de-assembling the cleaning device 1 in order to wash it or replace part of its components is another advantageous aspect also because it favours a correct disposal of the component to be replaced.

LEGEND OF FIGURE REFERENCES ear cleaning device 1
air dispenser 2
junction element 4
elastic bag 5
tip 6
hole 7
pressure areas 8
first hole 9
first end 10
second hole 11
second end 12
further hole 13
insertion portion 14
connecting portion 15
lobes 16
longitudinal axis L
convex wall 17
intermediate walls (grooves) 18
ribs 19

The invention claimed is:

1. An ear cleaning device comprising:
a fluid dispenser; and
a hollow cleaning body which is elongated according to a relative longitudinal axis and in communication with the fluid dispenser, wherein the cleaning body includes an insertion portion that is configured to assume a resting configuration defined as when the insertion portion is at least partially insertable in an ear canal, and wherein the insertion portion is configured to assume an expanded configuration defined as when the insertion portion has an increased volume due to expansion caused by fluid supplied by the dispenser;
wherein the insertion portion comprises:
a plurality of lobes which are elongated according to the longitudinal axis and form convex portions towards an outside of the insertion portion, wherein the plurality of lobes swell up when the insertion portion assumes the expanded configuration, and
a plurality of connecting walls positioned between lobes of the plurality of lobes, wherein the plurality of connecting walls develop along the longitudinal axis, forming grooves between the lobes,
wherein the plurality of connecting walls are configured to resist traction and torsional stresses to which the corresponding lobes are subjected to when the insertion portion is removed from the ear canal while the plurality of lobes are swelled up when the insertion portion assumes the expanded configuration.

2. The device according to claim 1, wherein the plurality of lobes includes a number of lobes equal to or greater than two.

3. The device according to claim 1, wherein the insertion portion assumes an ovoid shape in the expanded configuration, and wherein said grooves are configured to allow a flow of fluid from the ear canal to outside of the ear.

4. The device according to claim 1, wherein the cleaning body includes a connection portion that is in one piece with the insertion portion, and wherein the connection portion is connectable to the fluid dispenser.

5. The device according to claim 4, wherein the connection portion has a diameter that prevents the insertion of the connection portion into the ear canal.

6. The device according to claim 1, wherein the cleaning body comprises a material selected from the group consisting of elastic material, biocompatible silicone, elastomer material, latex, and rubber.

7. The device according to claim 1, wherein the fluid dispenser includes a manual pressure air delivery pump having an elastic bag on which the user can apply pressure.

8. The device according to claim 1, further comprising a junction element having an internal fluid passage pipe and a first end connectable to said fluid dispenser and having a second end connectable to said cleaning body.

9. The device according to claim 1, wherein at least said fluid dispenser and said cleaning body are separable from each other and can be re-assembled.

10. The device according to claim 1, wherein said device has a shape suitable for cleaning human ears or ears of animals.

11. The device according to claim 1, wherein each of the plurality of connecting walls has a thickness greater than a thickness of each of the plurality of lobes.

* * * * *